United States Patent
Nielsen

(10) Patent No.: US 6,171,594 B1
(45) Date of Patent: Jan. 9, 2001

(54) ADHESIVE AGENT AND USE OF SUCH AGENT

(75) Inventor: Inger Mann Nielsen, Frederiksberg (DK)

(73) Assignee: Colorplast A//S, Humlebaek (DK)

(*) Notice: Under 35 U.S.C. 154(b), the term of this patent shall be extended for 0 days.

(21) Appl. No.: 09/147,505

(22) PCT Filed: Jul. 2, 1997

(86) PCT No.: PCT/DK97/00291

§ 371 Date: Jan. 11, 1999

§ 102(e) Date: Jan. 11, 1999

(87) PCT Pub. No.: WO98/01167

PCT Pub. Date: Jan. 15, 1998

(30) Foreign Application Priority Data

Jul. 10, 1996 (DK) .................................................. 0772/96

(51) Int. Cl.⁷ .......................... A61K 35/78; A61L 15/16; A61M 31/00; A61F 13/02

(52) U.S. Cl. ....................... 424/195.1; 424/443; 424/445; 424/447; 424/448; 604/304; 604/307; 602/42; 602/43; 602/48; 602/49

(58) Field of Search .................... 424/195.1, 443, 424/444, 445, 447, 448, 449, 78.06; 524/22, 27, 45, 54, 55, 71, 274, 78; 604/304, 307; 602/42, 43, 48, 49

(56) References Cited

U.S. PATENT DOCUMENTS

| | | |
|---|---|---|
| 4,231,369 | 11/1980 | Sorensen et al. ...................... 604/336 |
| 4,350,785 | 9/1982 | Habib ....................................... 524/55 |
| 4,367,732 | 1/1983 | Poulsen et al. .......................... 602/56 |
| 4,551,490 | 11/1985 | Doyle et al. .............................. 524/22 |
| 4,675,009 * | 6/1987 | Hymes et al. ......................... 604/304 |
| 4,882,204 * | 11/1989 | Tenenbaum ........................... 427/180 |
| 4,917,890 | 4/1990 | McAnalley ......................... 424/195.1 |
| 4,959,214 | 9/1990 | McAnalley ......................... 424/195.1 |
| 4,966,892 | 10/1990 | McAnalley ............................. 514/54 |
| 5,266,318 * | 11/1993 | Taylor-McCord ................. 424/195.1 |
| 5,332,576 * | 7/1994 | Mantelle ............................... 424/443 |
| 5,405,366 * | 4/1995 | Fox et al. ............................... 607/50 |
| 5,409,703 * | 4/1995 | McAnalley et al. ................. 424/435 |
| 5,417,657 * | 5/1995 | Hauer ...................................... 604/96 |
| 5,420,114 | 5/1995 | Clodman et al. ....................... 514/23 |
| 5,487,899 * | 1/1996 | Davis ................................... 424/443 |
| 5,731,303 * | 3/1998 | Hsieh ................................... 514/183 |
| 5,760,102 * | 6/1998 | Hall et al. ............................ 523/120 |

FOREIGN PATENT DOCUMENTS

| | | |
|---|---|---|
| 0 048 556 | 3/1982 | (EP) . |
| 0 227 806 | 7/1987 | (EP) . |
| 0 328 775 | 8/1989 | (EP) . |
| 6-065073 | 3/1984 | (JP) . |
| 4-054107 | 2/1992 | (JP) . |
| 4-054108 | 2/1992 | (JP) . |
| 4-283511 | 10/1992 | (JP) . |
| WO89/10750 | 11/1989 | (WO) . |
| WO96/00094 | 1/1996 | (WO) . |

OTHER PUBLICATIONS

Tyler, V. Herbs of Choice, Pharmaceutical Products Press, pp. 155–157, 1994.*

Pearl, R. et al, "Early Local Complications From Intestinal Stomas", Arch. Surg., Oct. 1985, vol. 120, 1145–1147.

Hellman, J. et al, "Dermatological Complications In Colostomy And Ileostomy Patients", International Journal of Dermatology, Mar. 1990, vol. 29, No. 2, 129–133.

Grindlay, D. et al, "The Aloe vera Phenomenon: A Review Of The Properties And Modern Uses Of The Leaf Parenchyma Gel", Journal of Ethnopharmacology, 1986, 16, 117–151.

Davis, R. et al, "Processed Aloe vera Administered Topically Inhibits Inflammation", Journal of the American Podiatric Medical Association, Aug. 1989, vol. 79, No. 5, 395–397.

* cited by examiner

Primary Examiner—Christopher Tate
(74) Attorney, Agent, or Firm—Jacobson, Price, Holman & Stern, PLLC

(57) ABSTRACT

An adhesive agent for application to human or animal skin, preferably for use in connection with ostomy or incontinence appliances, comprises a pressure sensitive adhesive and optionally additives conventionally used in adhesives of this kind and parts of or extracts from Aloe vera. Such adhesive prevents or alleviates skin problems.

10 Claims, No Drawings

ADHESIVE AGENT AND USE OF SUCH AGENT

BACKGROUND OF THE INVENTION

1. Field of the Invention

The present invention relates to an adhesive agent for application to human or animal skin, a method of producing such adhesive agent and an adhesive paste for application to human or animal skin. Furthermore, the invention relates to the use of the adhesive agent for securing of ostomy appliances and sealing around an ostomy, for wound dressings, for securing of devices for collecting urine, wound drainage bandages, orthoses and prostheses and for protection of skin areas and parts of the body against pressure, impacts, friction and/or exudates from the body, and the use of the adhesive agent as an ostomy paste.

2. Description of the Related Art

Skin adhesive agents are today among other things, used for the above-mentioned purposes.

A widely used embodiment of skin adhesive agents comprises a pressure sensitive adhesive elastomeric matrix in which water absorbing and water-swellable particles of hydrocolloids are dispersed. The pressure sensitive adhesive matrix will adhere to skin and contribute to the cohesion of the adhesive. The water absorbing properties of the hydrocolloids enable adhesion to moist skin by removing moisture from the surface. As the hydrocolloids constantly absorb moisture emanating from the skin or originating from exuding wounds or from, e.g., a stoma, the hydrocolloids also contribute to securing a good adherence over extended periods of time and also prevent maceration of the skin.

In the fields of use mentioned above, the adhesive agents will come into contact with body fluids of different kinds: faces, urine, wound exudates, sweat et cetera. Existing skin adhesives often suffer from the drawback that the adhesiveness are destroyed by contact with body fluids. The parts of the adhesive being in direct contact with the skin or which is exposed to the body fluids will gradually swell due to the water absorbing and water-swelling properties of the hydrocolloids which will eventually cause a disintegration of the adhesive matrix.

Skin problems are common for persons having a stoma. Generally, about 40% have skin problems (Pearl et al. 1985 "Early local complications from intestinal stomas", Arch. Surg. 120; 1145–1147.) and the frequency is especially high for persons having an urostomy or ileostomy. About 80% of the persons having an ileostomy have skin problems (Hellman, J. D., Lago, C. P. 1990 "Dermatologic complications in colostomy and ileostomy patients", International Journal of Dermatology, 29 (2); 129–133.). The skin problems are mostly pronounced in a circular area around the stoma (½ inch from the stoma) (Hellman and Lago 1990).

Two common causes for skin problems are:
Inflammatory changes caused by cronical irritation and
Infection by bacteria and/or fungi.

Skin problems associated with an ostomy are different from skin problems generally associated with adhesives for skin (dressings or plasters) as the adhesives of ostomy appliances are placed permanently at the same site during long periods of time (cronical irritation) whereas other adhesives for skin are normally only placed at the same site for a short period of time.

It is desirable that the adhesives for use in connection with ostomy appliances are formulated so as to minimise the risk of skin problems and even more desirable if the adhesive might directly alleviate skin problems which have occurred.

During use in ostomy appliances it is observed that the adhesive agent around the stoma is often gradually eroded due to the disintegration of the adhesive giving access to the skin for the exudates. This is particularly a problem for ostomy patients having a urostomy or an ileostomy from which the exudates are fluid and aggressive. The result is that the risk of leakage increases as will the risk of direct contact between exudate and skin which may lead to severe skin problems and the ostomy appliance and with this, the adhesive will have to be changed more frequently than desired which again will stress the skin and cause higher expenses.

If the adhesive has been extensively eroded by aggressive exudates, the changing of the adhesive appliance may be rendered more inconvenient and laborious as left eroded adhesive will have to be removed mechanically which may cause further stress and strain to the skin. If optional remnants of adhesive are not removed entirely, they may hamper the adhering of the substitute appliance.

Similar problems may be encountered when using adhesive agents for wound drainage bandages or for bandages for use with cronical wounds or especially exuding wounds.

When bandaging wounds, contact between the adhesive and wound exudate will have a similar disintegrating effect on the adhesive leading to problems of the same kind as discussed above when changing the bandage, and furthermore, left parts of adhesive in the wound may affect the wound-healing process. In case of leakage, a further risk of contamination ana microbial infection of the wound exists.

Adhesive agents are also used for securing devices such as uridomas for collecting urine from incontinent males. In such an application, a similar risk of disintegration of the adhesive due to direct contact with urine exists and the direct contact between urine and skin may lead to similar problems as discussed above.

Adhesive agents are also used for securing orthoses and prostheses, e.g., breast prostheses, and for protection of skin areas or Darts of the body against pressure, impacts and/or friction. In these applications secretion of sweat will be the primary cause for swelling and disintegration of the adhesive agent and irritation of the skin leading to the inconveniences and problems mentioned above in connection with exchange of the appliance.

Typical examples of adhesives used as skin adhesives are the hydrocolloid adhesives disclosed in DK patent specifications Nos. 147,034 and 147,035 and in U.S. Pat. No. 4,551,490.

Adhesive pastes are especially used for filling cavities or irregularities in the skin around e.g., an ostomy in order to obtain a plane surface for adhesion of the adhesive for securing an ostomy appliance and for sealing between the adhesive agent and an ostomy. A paste is normally of a semi-liquid, more plastic consistency and may e.g., be based on a solution of a film forming polymer in which hydrocolloid particles are dispersed in an alcohol such as ethanol. Agents conventionally used for enhancing the adhesiveness may also be added. Such an adhesive agent may further comprise agents for regulating the viscosity and/or stabilisers and/or preservatives and such adhesives suffer from the same drawbacks as mentioned above.

Typical examples of the composition of adhesive agents are disclosed in DK patent specification No. 155.571 and EP patent specification No. 48.556.

Thus, there is still a need for an adhesive agent or paste having improved performance with respect to alleviating the skin problems caused by the action of aggressive exudates or excretions from a body.

BRIEF SUMMARY OF THE INVENTION

It has surprisingly been found that when adding Aloe vera to an adhesive agent for use in appliances to be used in connection with collection of exudates or excretions from a body, a better protection of the skin against the aggressive action of excretions from the body is achieved.

Thus, the invention relates, in its broadest aspect to an adhesive agent for application to human or animal skin comprising a pressure sensitive adhesive and optionally additives conventionally used in adhesives of this kind which adhesive agent comprises Aloe vera.

Furthermore, the invention relates to a method of producing such adhesive agent, and an adhesive paste for application to human or animal skin, to the use of such adhesive agent for securing of ostomy appliances and sealing around an ostomy, for wound dressings, for securing of devices for collecting urine, wound drainage bandages, orthoses and prostheses and for protection of skin areas and parts of the body against pressure, impacts, and friction, and/or exudates from the body and the use of the adhesive paste as an ostomy paste.

DETAILED DESCRIPTION OF THE INVENTION

The present invention relates to an adhesive agent for application to human or animal skin comprising a pressure sensitive adhesive and optionally additives conventionally used in adhesives of this kind which adhesive agent is characterised in that it comprises parts of or extracts from Aloe vera.

The basic idea is to add Aloe vera powder (prepared from Aloe vera gel) directly to the adhesive as a component which surprisingly has been found to prevent and alleviate skin problems for users of ostomy appliances.

When the adhesive absorbs moisture in the form of sweat, secretion from a stoma or a wound or a crack, or urine flowing into an uridoma, it swells and the Aloe vera components being soluble in water are released. In the area next to a stoma or an exuding wound the adhesive may be moistened to a considerable extent due to secretions from the stoma or wound and thus. Aloe vera will especially be released in the area next to the stoma or wound, exactly at the site having the most pronounced skin problems (Hellman and Lago 1990).

It is advantageous to add the Aloe vera as a component of the adhesive instead of applying an Aloe vera gel directly to the skin for the following reasons: it saves an operation, it is not necessary to await the evaporation of the water of an Aloe vera gel before placing the ostomy appliance or wound dressing(if the skin is not completely dry when placing the appliance, the adhesive will not obtain good adhesion to the skin), a reduction of the adhesion of the adhesive agent to the skin due to the presence of Aloe vera components on the skin is avoided, and a controlled release of Aloe vera from the adhesive is obtained giving the highest release in the most humid areas next to the stoma or wound where most of the skin problems occur.

Aloe vera is reported to have an antibacterial effect (Grindlay, D., Reynolds, T. 1986 "The Aloe vera phenomenon: A review of the properties and modern uses of the leaf parenchyma gel", Journal of Ethnopharmacology, 16; 117–151) and furthermore to have an anti-inflammatory effect (Davis, R. H., Rosenthal, K. Y., Cesario, L. R., Rouw, G. A. 1989 "Processed Aloe vera administered topical inhibits inflammation". Journal of the American Podiatric Medical Association. 79 (8); 395–397).

Nearly 200 species of Aloe exist. Only few of these do have commercial interest, among these Aloe vera (=A. Barbadensis). Aloe vera is a perennial plant having sturdy leaves of a weight of up to half a kilogram containing clear gel (colourless mucilaginous pulp) consisting of about 99.5% water.

The Aloe vera is commercially available in the form of a gel and in the form of a spray dried or freeze dried powder (dried gel) in various concentrations. Of most interest for the adhesives of the invention is Aloe vera gel in powder form as it may be mixed directly into the adhesive.

The natural gel comprises about 0.5% Aloe vera solids. A spray dried powder has a concentration 100× higher than the gel and a freeze dried powder a concentration 200× the concentration of the gel. Thus, freeze dried Aloe vera powder is 200 times as concentrated as the gel. Spray dried Aloe vera powder is "only" 100 times as concentrated as the natural gel because this powder comprises a carrier, typically malto-dextrin.

Japanese patent publication No. 4-54107 discloses a cosmetic product comprising an adhesive containing an Aloe extract and polyvinylpyrrolidone and/or a copolymer containing polyvinylpyrrolidone and a second component composed of a polymer or copolymer of acrylic acid and/or methacrylic acid which product is stated not to give harmful irritation to the skin.

Japanese patent publication No. 4-54108 discloses a cosmetic product comprising a plastic film and an adhesive containing an Aloe extract and polyvinylpyrrolidone and/or a copolymer containing polyvinylpyrrolidone and a second component comprising a low-molecular weight polyhydric alcohol having <2000 molecular weight which product is stated not to give harmful irritation to the skin.

Japanese patent publication No. 6-65073 discloses 2 water proof adhesive plaster having a waterproof backing and an adhesive layer comprising pharmaceutical, e.g., D,L-alpha-tocopherol, moistening the skin and giving continuous action of the drug component. The tacky adhesive layer contains a tacky adhesive and at least one kind of drug selected from dl-alpha-tocopnerol acetate, retinol acetate, retinol palmitate, biotin, panthothenic acid, olive oil. Aloe and rice bran.

Japanese patent publication No. 4-283511 discloses a two component skin plaster with durable adhesion and cooling sensation comprising a composition containing hydrogel and composition comprising water-soluble powdery substance. An aloe extract may be applied to the plaster.

U.S. Pat. Nos. 4,917,890, 4,959,214 and 4,966.892 as well as EP patent specifications Nos. 227,806 and 328,775 disclose gels containing an extract of Aloe vera and Carbopol® 940 for use in healing of wounds.

However, there is no indication nor suggestion to add Aloe vera to a hydrocolloid adhesive for use in ostomy or incontinence appliances or a wound dressing nor indication or suggestion that such addition should impart a better protection of the skin against the aggressive action of excretions from the body. Now it has surprisingly been found that an improved performance is obtained using adhesives comprising Aloe vera and a hydrocolloid.

Ostomy appliances comprising an adhesive according to the invention may be any appliance known per se, the difference being use of the adhesive of the invention. The appliances may be one-piece or two-piece appliances. Incontinence appliances comprising an adhesive according to the invention may be any appliance known per se, e.g., an urisheet or uridom. The adhesive may be placed directly on the sheeth or on a separate adhesive strip for securing the urisheeth to the penis. Wound dressings comprising an adhesive according to the invention may be any appliance known per se, e.g., wound dressings for cronic ulcers which may be in the form of larger plates or in the form of minor dressings adapted for treatment or prevention of cracks or fissures, callus or corns, or abrations.

The adhesive of the invention preferably comprises a plastic or elastomeric matrix having hydrocolloid particles dispersed therein.

The elastomeric matrix may e.g., be based on polyisobutylene, butyl gum, styrene blockcopolymers, polyacrylates or acrylate copolymers, silicone gum, natural gum, polyurethane gum, polyvinylether and mixtures thereof.

Additives conventionally used in additives for ostomy or incontinence appliances or wound dressings are e.g., additives for adjusting self-adhesive and cohesive properties of the matrix. Thus, it may be supplied with substances for promoting the adhesiveness, e.g., a resin, or emulsifiers, e.g., an oil, and/or antioxidants for protecting an elastomer against degradation or decomposition. Such additives are well known within the art and are, e.g., described in U.S. Pat. No. 4,551,490 and in DK Patent No. 147,035.

In accordance with one embodiment of the invention the adhesive matrix comprises a polyisobutylene and a hydrocolloid.

Such an adhesive typically comprises from 25 to 50% (w/w) polyisobutylene, from 0 to 20% (w/w) butyl rubber, from 0 to 15% (w/w) tackifying resin and from 25 to 55% (w/w) of hydrocolloid.

In accordance with another embodiment of the invention the adhesive matrix comprises a blockcopolymer comprising styrene and one or more olefins and/or dienes, e.g., olefins or dienes having 4–6 carbon atoms, preferably having 4 carbon atoms, such as 1-butene, isoprene or butadiene. The block copolymer may, e.g., be a styrene-isoprene copolymer or a styrene-butadiene-styrene copolymer.

Typically such an adhesive comprises from 5 to 30% (w/w) styrene-isoprene-styrene block copolymer, from 15 to 50% (w/w) tackifying resin and from 25 to 55% (w/w) of hydrocolloid, and from 0 to 25% (w/w) of plasticizer.

A plasticizer may be any conventional plasticizer for use together with the copolymer e.g., be a phthalate such as dioctyl phthalate or an adipate such as dioctyl adipate or an oil such as liquid paraffin.

The amount of Aloe vera present in the adhesive of the invention may be from 0.01 to 5% (w/w) which ensures a pain relieving effect, an enhancing effect on the healing of a wound, shows a marked antimicrobial activity and shows an anti-inflammatory effect.

The amount of Aloe vera is preferably from 0.3 to 3% (w/w).

Suitable hydrocolloids for use in such adhesives are naturally occurring hydrocolloids such as guar gum, locust bean gum, pectin, alginates, gelatine, xanthan or karaya gum, semisynthetic hydrocolloids such as cellulose derivatives, e.g. salts of carboxymethylcellulose, methylcellulose and hydroxypropylmethylcellulose, sodium starch glycollate and synthetic hydrocolloids such as polyvinyl pyrrolidone, polyvinyl alcohol, polyethylene glycol or certain polyacrylates. The hydrocolloid may be wholly or partly be constituted by psyllium material as disclosed in WO 96/00094.

The invention also relates to a method of producing an adhesive agent for application to human or animal skin, preferably for use in connection with ostomy or incontinence appliances comprising a pressure sensitive adhesive and optionally additives conventionally used in adhesives of this kind, the adhesive agent comprises parts of or extracts from Aloe vera which method comprises mixing, in a heated mixer, a plastic or elastic matrix-forming adhesive material and a part of a hydrocolloid material, turning off the heating, continuing the mixing for a short while, admixing the remaining part of the hydrocolloid material and Aloe vera and continuing the mixing in vacuo until a homogeneous mixture is obtained.

The invention further relates to a paste for application to human or animal skin, which paste comprises an adhesive agent for application to human or animal skin, preferably for use in connection with ostomy or incontinence appliances comprising a pressure sensitive adhesive and optionally additives conventionally used in adhesives of this kind, the adhesive agent comprises parts of or extracts from Aloe vera.

In another aspect, the invention relates to the use of an adhesive agent comprising Aloe vera and a hydrocolloid for securing ostomy appliances to the skin and for sealing around an ostomy, for securing wound dressings or wound drainage bandages to the skin, for securing devices for collecting urine to the skin, or for securing orthoses or prostheses to the skin.

Preferably, an adhesive agent comprising Aloe vera is used for securing of an ostomy appliances and sealing around an ostomy, for securing and sealing of devices for collecting urine or for securing orthoses and prostheses, preferably prostheses such as breast prostheses.

In a further aspect the invention relates to the use of an adhesive agent comprising Aloe vera for protection of skin areas and parts of the body against pressure, impacts and friction and/or the aggressive action of excretions from the body.

In accordance with yet another aspect, the invention relates to the use of an adhesive agent comprising Aloe vera as an ostomy paste.

The invention is illustrated more in detail in the below examples which are provided to illustrate presently-contemplated preferred embodiments and the best mode for practising the invention, but are not intended to be limiting thereof.

Materials and Methods

Polyisobutylene: Vistanex® LM-MH from Exxon Chemical

Sodium carboxymethylcellulose (CMC): Blanose® 9H4XF from Hercules

Freeze dried Aloe vera powder: C.E. Roeper

Experimental Part

EXAMPLE 1

Preparation of adhesive agent according to the invention
Adhesive agent No. 1

An adhesive agent according to the invention was prepared comprising 40% by weight of polyisobutylene, 20% Gelatine, 20% CMC, 19% Pectin and 1% freeze dried Aloe vera powder.

The adhesive was prepared in a Z-blade mixer. Before the mixing, the mixing chamber was heated to 80° C. by means of an oil heater. Polyisobutylene, Aloe vera powder and the hydrocolloids were weighed out separately. Firstly, half the amount of hydrocolloids and all the polyisobutylene were placed in the mixing chamber. The heat supply was turned off. Mixing took place for 1–2 minutes after which the remaining amount of hydrocolloids and the Aloe vera powder were added. Then the mixing was continued in vacuo until a total mixing time of 30 minutes. The adhesive agent was removed from the mixer and pressed into 1 mm thin plates between two sheets of silicon paper in a hydraulic press at 90° C. This adhesive agent was designated adhesive agent No. 1.

Preparation of adhesive agent without Aloe vera for comparison

Adhesive agent No. 2

An adhesive agent No. 2 was manufactured in a similar manner. This is a standard recipe for an ostomy adhesive agent and is directly comparable to adhesive agent no. 1, except for freeze dried Aloe vera powder.

Comparison of adhesive agent no. 1 and 2.

Standard laboratory tests have been carried out.

Tack test

In the tack test a Teflon probe of defined surface roughness ($R_a$=0.5) and area (6 mm diameter) is brought into contact with the adhesive at a controlled rate (50 mm/min), under a fixed pressure (3N) for a short time (2 seconds) and subsequently the bond formed between the probe and adhesive is broken, also at a controlled rate (500 mm/min). Tack is measured as the maximum force required in breaking the adhesive bond.

Peel test

The peel adhesion is defined as the force required to remove the adhesive, which has been applied to a standard test plate (Teflon, $R_a$=2) under specified conditions (23° C. and 50%RH) from the plate at a specified angle (90°) and speed (300 mm/min). The peel adhesion is measured 30 minutes after application of the adhesive to the test plate. The adhesive strips are 20 mm wide and have a minimum length of 175 mm in the machine direction. Peel adhesion is expressed in Newton per 20 mm.

Water absorption

Water absorption involves soaking adhesive strips into a 0.9% aqueous solution of sodium chloride under specified conditions (37° C.). Only one side of the adhesive is exposed to the aqueous solution. The absorption is calculated as the weight gain of the adhesive per square centimeter.

TABLE 1

Laboratory test results.

| Adhesive agent No. | Composition | Amount (Wt. %) | Tack (N) | Peel (N) | Water abs. (g/cm$^2$) |
|---|---|---|---|---|---|
| 1 | Polyisobutylene | 40 | 15 | 10 | 0 |
|   | Gelatine | 20 | | | |
|   | Pectin | 19 | | | |
|   | CMC | 20 | | | |
|   | Freeze dried Aloe vera | 1 | | | |
| 2 | Polyisobutylene | 40 | 14 | 10 | 0 |
|   | Gelatine | 20 | | | |
|   | Pectin | 20 | | | |
|   | CMC | 20 | | | |

As can be seen from Table 1, the laboratory test results are similar for adhesive agent no. 1 and 2. This means, that freeze dried Aloe vera powder added in an amount of 1% does not have any adverse effect on the adhesive properties.

EXAMPLE 2

Preparation of adhesive agents according to the invention

Adhesive agent No. 3

Adhesive agent No. 3 was manufactured in a similar manner as agent No. 1. The composition is stated in Table 2 below. Psyllium is a term for a water-absorbing, mucus forming material which is produced from the seeds from plants of the genus Plantago.

Adhesive agent No. 4

Adhesive agent No. 4 was manufactured in a similar manner as agent No. 1. The composition is stated in Table 2 below.

Preparation of adhesive agent without Aloe vera for comparison

Adhesive agent No. 5

Adhesive agent No. 5 was manufactured in a similar manner as agent No. 1. The composition is stated in Table 2 below.

Comparison of adhesive agent Nos. 3,4 and 5.

Testing of the time until first appearance of microbial contamination

The adhesive was placed in a moist atmosphere (100%RH) at 40° C. One side of the adhesive was uncovered and is thereby exposed to the moist atmosphere. The time until the first appearance of microbial contamination was determined by visual inspection of the exposed surface.

TABLE 2

Laboratory test results.

| Adhesive agent No. | Composition | Amount (Wt %) | Time until first microbial appearance |
|---|---|---|---|
| 3 | Polyisobutylene | 40 | ~48 hours |
|   | Psyllium | 59 | |
|   | Freeze dried Aloe vera | 1 | |
| 4 | Polyisobutylene | 40 | ~35 hours |
|   | Psyllium | 59.5 | |
|   | Freeze dried Aloe vera | 0.5 | |
| 5 | Polyisobutylene | 40 | less than 24 hours |
|   | Psyllium | 60 | |

It appears form Table 2 that Aloe vera has an anti-microbial effect in an adhesive according to the invention and that the effect is increasing with increasing concentration of Aloe vera. The anti-microbial effect is present after manufacturing the adhesive, which means that the heat used for the mixing of the adhesive is not destroying the active components in Aloe vera.

What is claimed is:

1. An adhesive composition useful for application to human or animal skin, comprising from 0.01 to 5% (w/w) parts of or extract from Aloe vera, from 25 to 50% (w/w) polyisobutylene, from 0 to 20% (w/w) butyl rubber, from 0 to 15% (w/w) tackifying resin and from 25 to 55% (w/w) of hydrocolloid.

2. An adhesive composition useful for application to human or animal skin, comprising from 0.01 to 5% (w/w) parts of or extract from Aloe vera, from 5 to 30% (w/w) styrene-isoprene-styrene copolymer, from 15 to 50% (w/w) tackifying resin, from 25 to 55% (w/w) of hydrocolloid and from 0 to 25% (w/w) of plasticizer.

3. The adhesive composition as claimed in claim 1 or 2 and further including a conventional adhesive additive.

4. The adhesive composition as claimed in claim 3, wherein said adhesive additive is selected from the group consisting of a resin, an emulsifier, an oil, an antioxidant, and another substance for promoting adhesiveness or protecting the composition from degradation or decomposition.

5. The adhesive composition as claimed in claim 1 or 2 wherein the content of parts of or extracts from Aloe vera is from 0.3 to 3% (w/w).

6. A method of producing an adhesive composition useful for application to human or animal skin, said adhesive composition comprising a pressure sensitive adhesive and parts of or extracts from Aloe vera, said method comprising mixing, in a heated mixer, a plastic or elastomeric matrix-forming adhesive material and a part of hydrocolloid particles, turning off the heating, continuing the mixing for a short while, admixing a remaining part of the hydrocolloid particles and a content of the parts of or extracts from Aloe vera which is from 0.01 to 5% (w/w), and continuing the mixing in vacuo until a homogeneous mixture is obtained.

7. A method for securing ostomy appliances to skin and for sealing around an ostomy, for securing wound dressings or wound drainage bandages to skin, for securing devices for collecting urine to skin, or for securing orthoses or prostheses to skin, comprising applying an adhesive composition to the skin, the adhesive composition comprising a pressure sensitive adhesive which comprises a plastic or elastomeric matrix having hydrocolloid particles dispersed therein wherein the adhesive composition comprises parts of or extracts from Aloe vera and wherein the content of parts of or extracts from Aloe vera is from 0.01 to 5% (w/w).

8. An ostomy appliance comprising an adhesive wafer for adhering to the skin which adhesive wafer comprises an adhesive composition as claimed in claim 1 or 2.

9. An incontinence appliance comprising an adhesive composition for adhering to the skin which adhesive composition comprises a pressure sensitive adhesive composition, the adhesive composition as claimed in claim 1 or 2.

10. A wound dressing comprising an adhesive composition for adhering to the skin which adhesive composition comprises a pressure sensitive adhesive and composition as claimed in claim 1 or 2.

* * * * *